United States Patent [19]

Tamura et al.

[11] Patent Number: 4,647,677

[45] Date of Patent: Mar. 3, 1987

[54] PROCESS FOR PREPARING 2,3-DIHYDRO-7-AMINOBENZOFURANS

[75] Inventors: Mitsuhiko Tamura; Haruo Katsumata, both of Kitakyushu; Takemi Nakanome, Sagamihara, all of Japan

[73] Assignee: Mitsubishi Chemical Industries Limited, Tokyo, Japan

[21] Appl. No.: 753,528

[22] Filed: Jul. 10, 1985

[30] Foreign Application Priority Data

Jul. 25, 1984 [JP] Japan .................................. 59-154458

[51] Int. Cl.$^4$ .......................................... C07D 307/79
[52] U.S. Cl. ..................................................... 549/462
[58] Field of Search ......................................... 549/462

[56] References Cited

U.S. PATENT DOCUMENTS

| | | | |
|---|---|---|---|
| 3,320,286 | 3/1965 | Franko-Filipasic | 549/462 |
| 3,356,690 | 12/1967 | Orwoll | 549/462 |
| 3,412,110 | 3/1965 | Scharpf | 549/462 |
| 4,499,306 | 2/1985 | Imaki et al. | 549/462 |

FOREIGN PATENT DOCUMENTS 205525  9/1956  Australia .

OTHER PUBLICATIONS

Gould, Mechanism and Structure in Org. Chemistry, Holt, Rinehart & Winston, N.Y., pp. 212–220 and 452–456 (1959).

*Primary Examiner*—Henry R. Jiles
*Assistant Examiner*—Bernard I. Dentz
*Attorney, Agent, or Firm*—Oblon, Fisher, Spivak, McClelland & Maier

[57] ABSTRACT

A process for preparing 2,3-dihydro-7-aminobenzofurans by reaction between 2,3-dihydro-7-halobenzofurans and ammonia in the presence of a copper catalyst, is described. The 2,3-dihydro-7-aminobenzofurans are useful as intermediates for insecticides.

13 Claims, No Drawings

PROCESS FOR PREPARING 2,3-DIHYDRO-7-AMINOBENZOFURANS

BACKGROUND OF THE INVENTION

This invention relates to a process for preparing 2,3-dihydro-7-aminobenzofurans.

DESCRIPTION OF THE PRIOR ART 2,3-Dihydro-2,2-dimethyl-7-benzofuranyl-N-methylcarbamate (carbofuran) is known as a useful insecticide. A variety of processes of preparing the carbofuran have been proposed. However, the known processes involve the problems that they have a number of steps, or they are poor in selectivity or yield. Accordingly, there is a demand of developing an improved process.

There has been proposed a process in which carbofuran is prepared through 2,3-dihydro-2,2-dimethyl-7-aminobenzofuran. U.S. Pat. No. 3,320,286 describes a process of preparing 2,3-dihydro-2,2-dimethyl-7-benzofuranol (hereinafter abbreviated as BFL), which is a precursor of the carbofuran, through the following sequence of reactions using o-nitrophenol and a methallyl halide as starting materials. In a reaction sequence, 2,3-dihydro-2,2-dimethyl-7-nitrobenzofuran is hydrogenated to give 2,3-dihydro-2,2-dimethyl-7-aminobenzofuran.

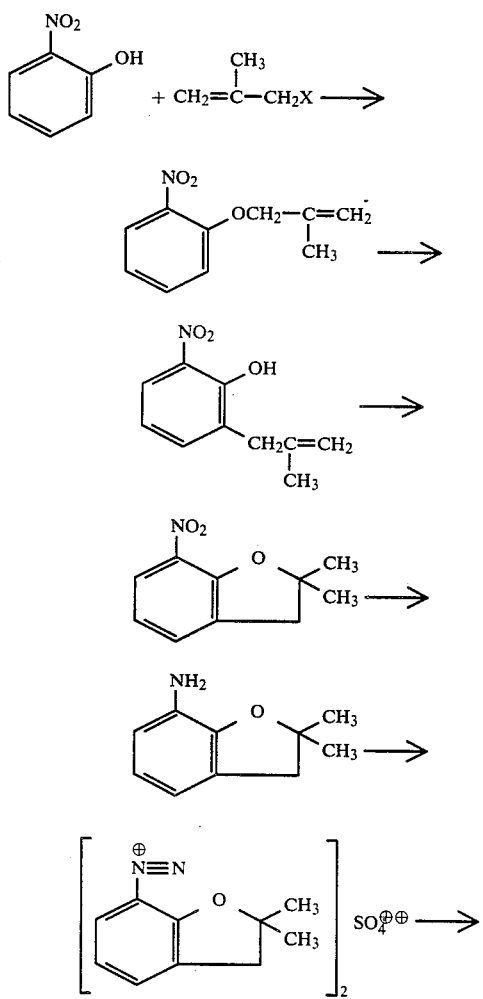

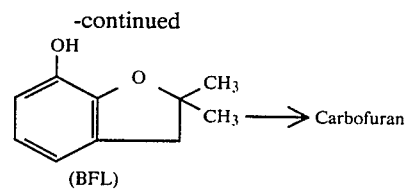

(BFL)

U.S. Pat. No. 3,412,110 teaches a process in which o-acetamidophenol and a methallyl halide are reacted in the same manner as mentioned above, to obtain 2,3-dihydro-2,2-dimethyl-7-acetamidobenzofuran, followed by hydrolysis to obtain 2,3-dihydro-2,2-dimethyl-7-aminobenzofuran.

On the other hand, for the introduction of an amino group into benzene ring, there is known a process in which ammonia is reacted, for example, with chlorobenzene in the presence of a copper catalyst to substitute the chlorine atom with the amino group. As is known, this reaction is a nucleophilic reaction, which is activated when there is an electron-attractive group, such as a nitro group, at the ortho or para position with respect to the chlorine atom. From this, it will be assumed that when an electron-donative group exists at the ortho position with respect to the chlorine atom, the reactivity decreases. The reaction between a compound having an electron-donative substituent at the ortho position relative to chlorine atom and ammonia has never been reported as far as we know.

We made studies to develop a novel process for preparing 2,3-dihydro-2,2-dimethyl-7-aminobenzofurans which are useful as an intermediate for carbofuran. For this purpose, a corresponding 7-halobenzofuran is used as a starting material. The furanyl group is a strongly electron-donative group and thus, the reaction between a halobenzofuran, in which the electron-donative furanyl group is connected at the ortho position to the halogen atom, and ammonia was considered to be very low in reactivity.

In the reaction of halobenzene with ammonia, the greater the plus charge of the carbon atom to which the halogen atom is bonded and the greater the minus charge of the halogen atom, the higher is the reactivity. As to 2,3-dihydro-2,2-dimethyl-7-chlorobenzofuran, the plus charge of the carbon atom to which the chlorine atom is bonded is reduced to ½–⅓ and minus charge of the chlorine atom is reduced to at a rate of 10–20%, respectively, compared with those of chlorobenzene.

To a surprise, however, we succeeded in obtaining 7-aminobenzofuran derivatives in high yield by reaction between corresponding 7-halobenzofuran derivatives and ammonia.

SUMMARY OF THE INVENTION

It is therefore an object of the present invention to provide a novel process for preparing 2,3-dihydro-7-aminobenzofurans which are useful as intermediates for carbofuran insecticides.

According to the present invention, there is provided a process for preparing a 2,3-dihydro-7-aminobenzofuran compound of the formula (1)

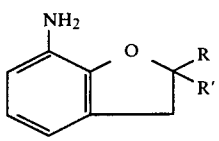

(1)

In which R and R' independently represent a hydrogen atom or a lower alkyl group, which comprises reacting a 2,3-dihydro-7-halobenzofuran of the formula (2)

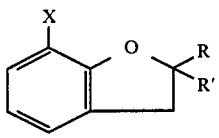

(2)

in which X represents a halogen atom, and R and R' have, respectively, the same meanings as defined above, with ammonia in the presence of a copper catalyst.

DETAILED DESCRIPTION AND EMBODIMENTS OF THE INVENTION

One of the starting compounds is a compound of the formula (2) in which R and R' may be the same or different and represent a hydrogen atom, or a lower alkyl group such as methyl, ethyl or propyl and X represents a halogen such as chlorine, bromine or iodine. Specific and preferable examples of the compound of the formula (2) include 2,3-dihydro-2,2-dimethyl-7-chlorobenzofuran and 2,3-dihydro-2,2-dimethyl-7-bromo-benzofuran. The compounds of the formula (2) are prepared, for example, according to the process described in U.S. Pat. No. 3,356,690. In the process, o-bromophenol and a methallyl halide are reacted to obtain 1-methallyloxy-2-bromobenzene, followed by rearrangement to obtain 2-bromo-6-methallylphenol. Subsequently, the 2-bromo-6-methallylphenol is heated in the presence of an appropriate acid catalyst to obtain 2,2-dimethyl-2,3-dihydro-7-bromobenzofuran. A variety of compounds included within the scope of the general formula (2) can be prepared according to the above process in which o-chlorophenol is used instead of o-bromophenol and/or an alkenyl halide such as allyl halide is used instead of the methallyl halide.

Alternatively, the compounds of the general formula (2) are prepared according to the process described in EP 90976. More particularly, cyclohexanone and an aldehyde such as isobutyl aldehyde are subjected to aldol condensation and dehydrated to obtain 2-isobutylidene cyclohexanone. This compound is halogenated and then dehydrohalogenated to 2-isobutenyl-6-chlorophenol, followed by cyclization to obtain 2,2-dimethyl-2,3-dihydro-7-halobenzofuran. Using propyl aldehyde instead of isobutyl aldehyde in the above process, 2-methyl-2,3-dihydro-7-halobenzofuran is obtained.

For the reaction between the compound of the formula (2) and ammonia, it is possible to feed gaseous ammonia to a reactor under pressure, or to cool gaseous ammonia for liquefaction in a reactor and use it for the reaction. However, the use of gaseous ammonia is not practically convenient. In general, liquid ammonia or aqueous ammonia solution is used, of which an aqueous ammonia solution is preferred. The concentration of ammonia in the solution may be from 1 to 100%, preferably from 5 to 70% by weight.

The amount of ammonia is 0.5 to 10 moles, preferably from 1 to 5 moles per mole of the compound of the general formula (2), calculated as $NH_3$.

The copper catalyst used for the reaction includes, for example, mono and divalent copper, their oxides, hydroxides, mineral acid salts such as hydrochlorides, sulfates, nitrates, phosphates and the like, and ammonia complex salts thereof.

The amount of the catalyst is in the range of from 0.01 to 2 moles, preferably from 0.05 to 1 mole, per mole of the compound of the formula (2).

The reaction system may be either uniform or non-uniform and the reaction is usually effected in the absence of solvent. However, if necessary, hydrocarbon solvents such as benzene, toluene and the like may be used.

The reaction is carried out at a temperature of from 150° to 400° C., preferably from 150° to 300° C. for a time of from 5 minutes to 10 hours, preferably from 30 minutes to 8 hours under a pressure self-produced at the reaction temperature.

When an aqueous ammonia solution is used in the process of the invention, the reaction system consists of an aqueous phase and an organic phase. In this system, the catalyst forms an ammonia complex salt, which is soluble in water or is partially in the form of an insoluble solid. The starting material and the reaction product are present in the organic phase.

And ammonium halide resulting from the reaction is also in water phase. So after the reaction, the insoluble solid catalyst is removed, then the organic phase is recovered by separation from the water phase or by the extraction from the reaction mixture with an organic solvent such as benzene, toluene and the like. The organic phase thus recovered is, washed with water if necessary, distilled to isolate the intended product and the product is, if necessary, purified by recrystallization from hexane, heptane and the like.

When it is difficult to isolate the product by distillation because of the slight difference of the boiling points between the product and the starting material, the organic phase is added an aqueous solution of a mineral acid such as hydrochloric acid, sulfuric acid to transfer the product into the water phase. Then the water phase is separated and neutralized by addition of an alkali to liberate the organic phase again. The organic phase, second occurrence, is separated or extracted with benzene, toluene and the like as above, then distilled to obtain the product. While, the starting material and the compound of the formula (3) are recovered by the distillation of the organic phase separated from the aqueous mineral acid solution. In some cases precipitation method is applied instead of distillation.

Since an aqueous ammonia solution is used, water essentially exists in the reaction system. This may involve hydrolysis or simultaneous reactions of the amino compound of the formula (1), thereby secondarily producing a hydroxy compound of the following formula (3). The amount of the side product is generally in the range of from 5 to 20 wt % of the compound of the formula (1).

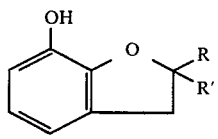

(3)

in which R and R' have, respectively, the same meanings as defined in formula (2).

Preparation of an insecticide, such as carbofuran, from the amino compound of the invention involves formation of a compound of the formula (3) through diazotization and hydrolysis, so that it is not necessarily required to separate the secondarily produced compound of the formula (3).

On the other hand, when liquid ammonia is used as a source for ammonia, an excess of ammonia in the reaction system is recovered in the form of a gas after completion of the reaction. If necessary, an aqueous acid solution is added to neutralize to the reaction solution and the catalyst is separated from the reaction solution, followed by treating the organic phase in the same manner as described before, thereby obtaining an intended product. The organic phase obtained after the separation of the catalyst may be extracted with an aqueous sulfuric acid solution. In this case, the amino compound of the formula (1) is converted to a sulfate and extracted in the aqueous phase. This aqueous phase is separated, followed by addition of sodium nitrite for diazotization and hydrolysis to obtain hydroxy compound of the formula (3).

In accordance with a preferred embodiment of the invention, 2,3-dihydro-2,2-dimethyl-7-chloro or bromo-benzofuran and an aqueous ammonia solution are reacted, without use of any solvent, at a temperature of from 150° to 400° C., preferably from 200° to 300° C. for 2,3-dihydro-2,2-dimethyl-7-chlorobenzofuran and from 150° to 300° C. for bromo-analogue. The concentration of the ammonia solution is from 5 to 70 wt %, and the amount of the ammonia solution is from approximately 1 to 5 times by mole the 2,3-dihydro-2,2-dimethyl-7-halobenzofuran, calculated as $NH_3$.

The reaction pressure is self-produced pressure, that is when reaction is carried at about 165° C., the self-produced pressure is about 9 kg/cm²G, and at 200° C., the pressure is about 20–25 kg/cm²G.

The present invention is described in detail by way of examples, which should not be construed as limitation of the invention.

EXAMPLES 1–5

0.1 mole of 2,2-dimethyl-2,3-dihydro-7-chlorobenzofuran, 0.3 mole of an aqueous 10% ammonia solution, calculated as $NH_3$, and 0.2 mole of each of copper catalysts indicated in Table 1 were charged into a 300 ml stainless steel reactor. Thereafter, the reactor was placed on an oil bath of 250° C. and was heated under agitation. After about 40 minutes, the pressure in the reactor reached a self-produced pressure of 40 kg/cm². The reaction mixture was maintained at the above-indicated temperature for further 2 hours. After completion of the reaction, the reaction mixture was cooled down to normal temperatures, and filtered to separate the catalyst therefrom, followed by separation into two phases. The resultant organic phase was analyzed by liquid chromatography to obtain the results indicated in Table 1.

EXAMPLES 6–7

The general procedure of Example 1 was repeated expect that the reaction conditions were partly changes as indicated in Table 1. The results are also shown in Table 1.

COMPARATIVE EXAMPLE

The procedure of Example 7 was repeated except that the reaction was effected for 5 hours without use of any catalyst. As a result, almost all the amount of the starting materials was recovered. The results are shown in Table 1.

Abbreviations and analysis conditions for the respective compound in Table are summarized below.
BFC: 2,2-dimethyl-2,3-dihydro-7-chlorobenzofuran
BFA: 2,2-dimethyl-2,3-dihydro-7-aminobenzofuran
BFL: 2,2-dimethyl-2,3-dihydro-7-benzofuranol
Analysis conditions (liquid chromatography)
Column: Nucleosil ODS 7 μm, 4 mmφ×30 cm
Mobile phase: 0,01 M sodium laurylsulfate in 50% aqueous acetonitrile solution (pH adjusted to 2.0 using phosphoric acid)
Flow rate: 1.0 ml/minute
Detector: UV 290 nm
Internal standard: dimethyl terephthalate
Retention time:
  BFL 5.6 minutes
  BFA 6.7 minutes
  IS 7.9 minutes
  BFC 15.9 minutes

TABLE 1

| | Reaction Condition | | | | | Results of Reaction | | | |
| | NH₃:Catalyst:BFC (molar ratio) | | | Temp. (°C.) | Time (hrs) | Catalyst | Reaction Rate of BFC (%) | Selectivities to | | |
| | | | | | | | | BFA (%) | BFL (%) | BFA + BFL (%) |
| Ex. No. | | | | | | | | | | |
| 1 | 3.0 | 0.2 | 1 | 250 | 2 | Cu₂O | 33.1 | 71.5 | 12.5 | 84.0 |
| 2 | " | " | " | " | " | CuCl₂ | 29.7 | 91.8 | 7.3 | 99.1 |
| 3 | " | " | " | " | " | CuSO₄ | 47.7 | 82.0 | 9.6 | 91.6 |
| 4 | " | " | " | " | " | Cu(NO₃)₂ | 49.5 | 60.1 | 4.8 | 64.9 |
| 5 | " | " | " | " | " | CuO | 47.2 | 63.8 | 9.5 | 73.3 |
| 6 | " | 0.5 | " | 225 | 5 | CuCl | 64.5 | 78.8 | 4.7 | 83.5 |
| 7 | " | 0.2 | " | 250 | " | CuSO₄ | 66.2 | 74.0 | 6.5 | 80.5 |
| Com. Ex. | 3.0 | — | 1 | 250 | 5 | — | 1.5 | 1> | 1> | 1> |

What is claimed is:

1. A process for preparing 2,3-dihydro-7-aminobenzofurans of the formula (1)

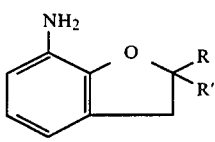

in which R and R' independently represent a hydrogen atom or a lower alkyl group which comprises: reacting a 2,3-dihydro-7-halobenzofuran of the formula (2)

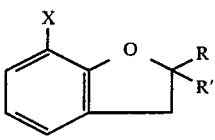

in which X represents a halogen atom, and R and R' have, respectively, the same meanings as defined above, with ammonia in the presence of a copper catalyst.

2. The process according to claim 1, wherein said ammonia is in the form of an aqueous solution having a concentration of from 1 to 100% by weight.

3. The process according to claim 1, wherein the reaction between the 2,3-dihydro-7-halobenzofuran of the formula (2) and ammonia is effected at a temperature of from 150 to 400° C.

4. The process according to claim 3, wherein the reaction is effected at a temperature of from 150° to 300° C.

5. The process according to claim 1, wherein said 2,3-dihydro-7-halobenzofuran of the formula (2) is 2,3-dihydro-2,2-dimethyl-7-chlorobenzofuran.

6. The process according to claim 1, wherein said copper catalyst is a member selected from the group consisting of copper oxides, hydroxides, chlorides, sulfates, nitrates, phosphates and ammonia complex salts.

7. The process according to claim 1, wherein the reaction is conducted in liquid ammonia.

8. The process according to claim 2, wherein the concentration of ammonia in solution ranges from 5 to 70% by wt.

9. The process according to claim 1, wherein the amount of ammonia percent ranges from 0.5 to 10 moles per mole of said 2,3-dihydro-7-halobenzofuran.

10. The process according to claim 9, wherein the amount of said ammonia ranges from 1 to 5 moles.

11. The process according to claim 1, wherein the amount of said catalyst ranges from 0.01 to 2 moles per mole of said 2,3-dihydro-7-halobenzofuran.

12. The process according to claim 11, wherein the amount of said catalyst ranges from 0.05 to 1 mole.

13. The process according to claim 1, wherein after said reaction, the insoluble catalyst is removed from the reaction medium, and the organic phase of the reaction medium is recovered.

* * * * *